(12) United States Patent
Boyer et al.

(10) Patent No.: US 9,159,148 B2
(45) Date of Patent: Oct. 13, 2015

(54) SYSTEM, METHOD, AND SOFTWARE FOR DISPLAYING PARAMETER VALUES WITH HISTORICAL RANGES

(71) Applicant: Covidien LP, Mansfield, MA (US)

(72) Inventors: Robert Boyer, Longmont, CO (US);
John Trenouth, Vancouver (CA);
Richard Batch, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 164 days.

(21) Appl. No.: 13/663,066

(22) Filed: Oct. 29, 2012

(65) Prior Publication Data

US 2013/0106864 A1  May 2, 2013

Related U.S. Application Data

(60) Provisional application No. 61/554,613, filed on Nov. 2, 2011.

(51) Int. Cl.
*G06T 11/20* (2006.01)
*G06F 19/00* (2011.01)

(52) U.S. Cl.
CPC .......... *G06T 11/206* (2013.01); *G06F 19/3412* (2013.01); *G06F 19/3418* (2013.01)

(58) Field of Classification Search
None
See application file for complete search history.

(56) References Cited

U.S. PATENT DOCUMENTS

| | | | | |
|---|---|---|---|---|
| 6,956,572 | B2 * | 10/2005 | Zaleski | 345/440.2 |
| 8,217,946 | B2 * | 7/2012 | Halpern et al. | 345/440 |
| 8,279,226 | B2 * | 10/2012 | Krieftewirth | 345/440.1 |
| 2005/0209515 | A1 * | 9/2005 | Hockersmith et al. | 600/316 |
| 2006/0200009 | A1 * | 9/2006 | Wekell et al. | 600/300 |
| 2011/0201911 | A1 * | 8/2011 | Johnson et al. | 600/365 |
| 2012/0001920 | A1 * | 1/2012 | Halpern et al. | 345/440.2 |

FOREIGN PATENT DOCUMENTS

| | | | |
|---|---|---|---|
| WO | 2004017831 | A1 | 3/2004 |
| WO | 2008002525 | A2 | 1/2008 |
| WO | 2009132434 | A1 | 11/2009 |

* cited by examiner

*Primary Examiner* — Ryan R Yang
(74) *Attorney, Agent, or Firm* — Carter, DeLuca, Farrell & Schmidt, LLP

(57) ABSTRACT

A method for patient monitoring includes receiving one or more first patient parameters from at least one medical device. The method further includes transforming the one or more first patient parameters into one or more gauge display parameters. The method further includes generating data operable to display the one or more gauge display parameters individually in a particular portion of a display device. The one or more gauge display parameters include at least a historical range and a current value within the historical range. The method further includes analyzing one or more second patient parameters to adjust the one or more gauge display parameters.

18 Claims, 4 Drawing Sheets

SYSTEM, METHOD, AND SOFTWARE FOR DISPLAYING PARAMETER VALUES WITH HISTORICAL RANGES

CROSS-REFERENCE TO RELATED APPLICATIONS

This application claims the benefit of priority under 35 U.S.C. §119(e) of U.S. Provisional Patent Application Ser. No. 61/554,613 entitled "DISPLAYING PARAMETER VALUES WITH HISTORICAL RANGES," which was filed on Nov. 2, 2011.

TECHNICAL FIELD

The present disclosure relates generally to patient monitoring, and more particularly to a system, method, and software for displaying parameter values with historical ranges.

BACKGROUND

When monitoring a patient, a medical device may collect and display information about that patient. The medical device may collect information through one or more of a variety of ways, such as a patient interface that measures a physiological condition, or a user interface that collects information input by a user. One may rely on this information to assess and treat the health of the patient.

SUMMARY

According to the present disclosure, disadvantages and problems associated with previous techniques for monitoring patients may be reduced or eliminated.

In certain embodiments, a method for patient monitoring includes receiving one or more first patient parameters from at least one medical device. The method further includes transforming the one or more first patient parameters into one or more gauge display parameters. The method further includes generating data operable to display the one or more gauge display parameters individually in a particular portion of a display device. The one or more gauge display parameters include at least a historical range and a current value within the historical range. The method further includes analyzing one or more second patient parameters to adjust the one or more gauge display parameters.

Certain embodiments of the present disclosure may provide one or more technical advantages. At a high level, embodiments of the disclosure relate to displaying a visual representation of historical parameter values and current parameter values. Some embodiments of the disclosure relate to visually representing a parameter value that is associated with a ventilator operation. The parameter value is displayed relative to representations of predetermined limits, as well as a range of parameter values that have been observed over a period of time. Embodiments of the disclosure can include different combinations of the features and components described herein, additional features or components that are not described herein. For example, in some embodiments, aspects of the visual representation can be used to display parameter values corresponding to other parameters such as, for example, SpO2 levels, pulse rate, and the like. All such implementations are considered to be within the ambit of the disclosure.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

Figure 1:
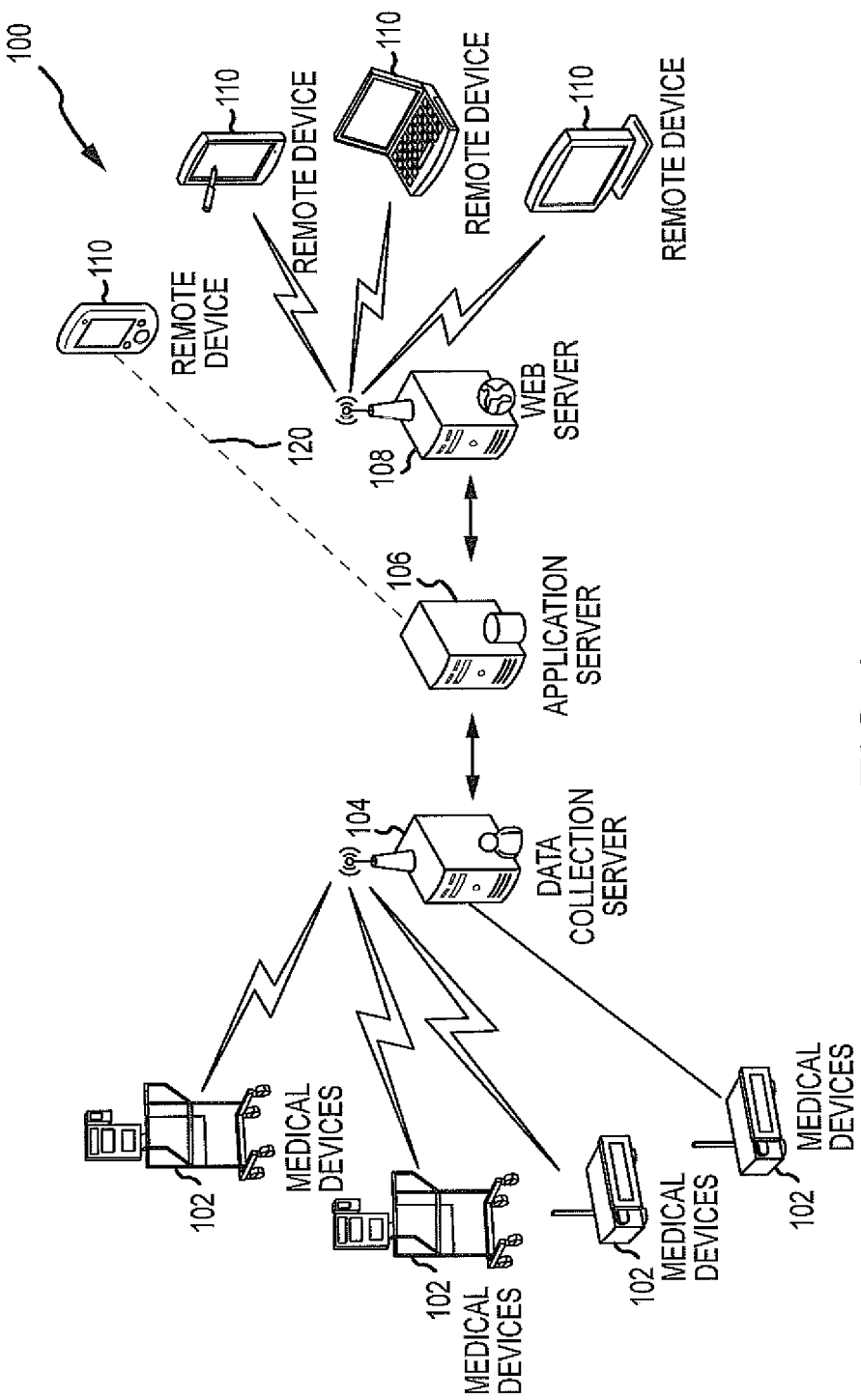
FIG. 1 illustrates an example system for patient monitoring, according to certain embodiments of the present disclosure.

FIG. 1 illustrates an example system 100 for patient monitoring, according to certain embodiments of the present disclosure. System 100 includes one or more medical devices 102, a data collection server 104, an application server 106, a web server 108, and one or more remote devices 110. Although this particular implementation of system 100 is illustrated and primarily described, the present disclosure contemplates any suitable implementation of system 100 according to particular needs.

According to one embodiment, system 100 is operable to monitor medical devices 102 and transform patient parameters into gauge display parameters. In certain embodiments, medical devices 102 generate patient parameters or store patient parameters input by a user. Patient parameters may refer to any patient identifiers, medical history, clinician notes, alarm thresholds, alarm events, device settings, measurements of values indicating physiological conditions such as oxygen saturation levels, pulse rates, heart rates, other vital signs, and any other output data from medical devices 102. Each medical device 102 may be connected to data collection server 104, which stores the patient parameters in a database. Application server 106 retrieves the patient parameters from the database and processes the patient parameters into gauge display parameters for web server 108. Remote devices 110 request and receive the gauge display parameters and display the gauge display parameters through a browser and/or native application on remote devices 110, thereby enabling clinicians using the remote devices 110 to view the gauge display parameters in remote locations. As described in more detail below, embodiments of the disclosure relate to gauge display parameters that include a visual representation of historical parameter values and current parameter values. Some embodiments of the disclosure relate gauge display parameters that include a visual representation of a parameter value that is associated with a ventilator operation. The parameter value is displayed relative to representations of predetermined limits, as well as a range of parameter values that have been observed over a period of time.

System 100 may include one or more medical devices 102. Medical devices 102 may be any devices that are used for tracking or treating patients. For example, medical devices 102 may include a ventilator connected to a patient to deliver respiration therapy. As another example, medical devices 102 may include a pulse oximeter that monitors the oxygen saturation of a patient's blood. As another example, medical devices 102 may include a device for tracking a patient without monitoring physiological conditions. In short, medical devices 102 may include any suitable combination of software, firmware, and hardware used to support any medical function. It should be noted that any suitable number of medical devices 102 may be included in system 100. In addition, there may be multiple groups of medical devices 102 in system 100.

According to one embodiment, in addition to performing a medical function, medical devices 102 may generate output data tracked by medical devices 102. For example, the ventilator may generate entries indicating the average volume of air expelled in each breath. The ventilator may generate entries identifying the parameter settings used by the ventilator and whether any alarms have been triggered. The ventilator may store the generated entries in local memory and output the entries. In some embodiments, medical devices may generate output data that is related to tracking patient identifications or locations, without necessarily generating data related to a physiological condition. In certain embodiments, medical devices 102 may output data in response to a data request. In certain other embodiments, medical devices 102 may constantly stream output data. In these embodiments, medical devices 102 may require an initial start signal or request signal prior to streaming data.

Medical devices 102 may be communicatively coupled to data collection server 104 via a network, according to one embodiment. The network facilitates wireless or wireline communication. The network may communicate, for example, IP packets, Frame Relay frames, Asynchronous Transfer Mode (ATM) cells, TDMA, CDMA, voice, video, data, and other suitable information between network addresses. The network may include one or more personal area networks (PANs), local area networks (LANs), radio access networks (RANs), metropolitan area networks (MANs), wide area networks (WANs), all or a portion of the global computer network known as the Internet, and/or any other communication system or systems at one or more locations. In certain embodiments, medical devices 102 may be communicatively coupled to other suitable devices including data collection server 104, application server 106, web server 108, and remote devices 110. In certain embodiments, data collection server 104 may be connected to other similar data collection servers in a particular format, such as a daisy-chain connection format.

System 100 may include one or more data collection servers 104, referred to primarily in the singular throughout this disclosure. Data collection server 104 may include one or more electronic computing devices operable to receive, transmit, process, and store data associated with system 100. For example, data collection server 104 may include one or more general-purpose PCs, Macintoshes, workstations, mainframes, server computers, one or more server pools, or any other suitable hardware. In addition, data collection server 104 may use any suitable operating system such as Windows, Apple, Linux, UNIX or any future operating system. In certain embodiments, data collection server 104 includes a web server. In short, data collection server 104 may include any suitable combination of software, firmware, and hardware. Although a single data collection server 104 is illustrated, the present disclosure contemplates system 100 including any suitable number of data collection servers 104. Moreover, although referred to as a data collection server, the present disclosure contemplates data collection server 104 comprising any suitable type of processing device or devices.

According to one embodiment, data collection server 104 receives patient parameters from medical devices 102. For example, data collection server 104 may request patient parameters from medical device 102 and receive patient parameters from medical device 102 in response to the request. As another example, data collection server 104 may receive streamed output data from a medical device 102. As another example, data collection server 104 may be configured to periodically request new data from medical device 102. Data collection server 104 may map the received patient parameters to match internal fields in the database and then transmit the data to a database, according to one embodiment. The stored data may be accessed by application server 106.

System 100 may include one or more application servers 106, referred to primarily in the singular throughout this disclosure. Application server 106 may include one or more electronic computing devices operable to receive, transmit, process, and store data associated with system 100. For example, application server 106 may include one or more general-purpose PCs, Macintoshes, workstations, mainframes, server computers, one or more server pools, or any other suitable hardware. In addition, application server 106 may use any suitable operating system such as Windows, Apple, Linux, UNIX or any future operating system. In short, application server 106 may include any suitable combination of software, firmware, and hardware. Although a single application server 106 is illustrated, the present disclosure contemplates system 100 including any suitable number of application servers 106. Moreover, although referred to as an application server, the present disclosure contemplates application server 106 comprising any suitable type of processing device or devices.

According to one embodiment, application server 106 creates a data service that runs on a conventional web services platform for transmitting data to web server 108. Application server 106 may include a database server in certain embodiments. According to one embodiment, application server 106 may include a logical system that may execute an algorithm, such as a clinical application using patient parameters including first patient parameters. For example, application server 106 may create gauge display parameters using first patient parameters, and those gauge display parameters are transmitted to web server 108. Application server 106 may maintain an activity log that logs data requests from remote devices 110 to track certain activities performed at remote devices 110. Therefore, if a clinician selects a particular patient representation to zoom in and view ventilator data specific to that patient, that selection may trigger a data request that is logged by application server 106. For example, when creating the gauge display parameters, application server 106 may compare the current parameter settings of the ventilator, as indicated by entries in the patient parameter set, to prior parameter settings. If any changes are detected, application server 106 may flag those changes for presentation to users on remote devices 110. Specifically, application server 106 may create data causing the depiction of the changed gauge display parameters on remote devices 110 to change color in response to receiving second patient parameters. Second patient parameters may include new parameters, for example, parameters associated with an additional machine or patient being monitored. Second patient parameters may further include changed patient parameters, such as a change in a temperature of a patient. Application server 106 may create additional gauge display parameters that cause a pop-up window to appear on the mobile device when any of the changed gauge display parameters are selected. The pop-up window may list all of the changed gauge display parameters and provide a single button through which a user may indicate that the changed gauge display parameters have been viewed. If that button is activated, the mobile device may transmit a message to application server 106 by way of web server 108 and application server 106 may then unflag those gauge display parameters, such that the depiction of those patient parameters on remote device 110 may return to the original color. In certain embodiments, application server 106 may transmit data directly to remote devices 110.

System 100 may include one or more web servers 108, referred to primarily in the singular throughout this disclosure. Web server 108 may include one or more electronic computing devices operable to receive, transmit, process, and store data associated with system 100. For example, web server 108 may include one or more general-purpose PCs, Macintoshes, workstations, mainframes, server computers, one or more server pools, or any other suitable hardware. In addition, web server 108 may use any suitable operating system such as Windows, Apple, Linux, UNIX or any future operating system. In short, web server 108 may include any suitable combination of software, firmware, and hardware. Although a single web server 108 is illustrated, the present disclosure contemplates system 100 including any suitable number of web servers 108. Moreover, although referred to as a web server, the present disclosure contemplates web server 108 comprising any suitable type of processing device or devices.

According to one embodiment, web server 108 creates a data service that runs on a conventional web services platform for receiving data from application server 106 and transmitting data to remote devices 110. For example, web server 108 may receive gauge display parameters from application server 106 and transmit, upon request in certain embodiments, to remote devices 110.

System 100 may include one or more remote devices 110. Remote devices 110 may be any device that provides output to and can receive input from a user, such as a clinician. Each remote device 110 may include one or more computer systems at one or more locations. In certain embodiments, output at remote devices may include vibrations, display views including pop-up messages, sound, or any combination desired. In some embodiments, remote devices 110 may connect to application server 106 through a direct socket connection, as indicated by reference number 120 in FIG. 1. Each computer system may include any appropriate input devices (such as a keypad, touch screen, mouse, or other device that can accept input), output devices, mass storage media, or other suitable components for receiving, processing, storing, and communicating data. Both the input device and output device may include fixed or removable storage media such as a magnetic computer disk, CD-ROM, or other suitable media to both receive input from and provide output to a user. Each computer system may include a personal computer, workstation, network computer, kiosk, wireless data port, personal data assistant (FDA), one or more processors within these or other devices, or any other suitable processing device.

According to one embodiment, remote devices 110 display one or more web pages hosted by application server 106 and/or web server 108 with gauge display parameters related to the patient parameters from medical devices 102. For example, a clinician may activate a browser on remote device 110 and navigate to a web page hosted by web server 108. The browser may render the web page, which includes gauge display parameters generated by application server 106. The web page may provide a summary of all medical devices 102 under a clinician's responsibility. In addition, the web page may enable a detailed view that displays specific device data, therapy parameter data, and alarm status data.

Although FIG. 1 depicts separate devices for data collection server 104, application server 106, and web server 108, it will be readily apparent that the functions of these devices may be combined into a single device that receives patient parameters from medical devices 102 and transforms the patient parameters into gauge display parameters. It will also be understood that this single device may alternatively transmit the gauge display parameters to remote device 110.

It will also be understood that the functions may be allocated differently than shown, with application server 106 additionally performing the functions of web server 108 or the functions of data collection server 104. In another embodiment, a single device may receive patient parameters, transform those patient parameters into gauge display parameters, and display the gauge display parameters on a screen.

A user of system 100 may detect patient conditions by examining parameters on remote device 110. The user, however, may be interested in understanding a relationship between historical parameter values and current parameter values. In certain embodiments of the disclosure, the user may access, examine, and manipulate the display of historical parameter values and current parameter values with gauge display parameters. Further details regarding how a user may access, examine, and manipulate gauge display parameters are described with reference to FIGS. 2-4 below.

Figure 2:
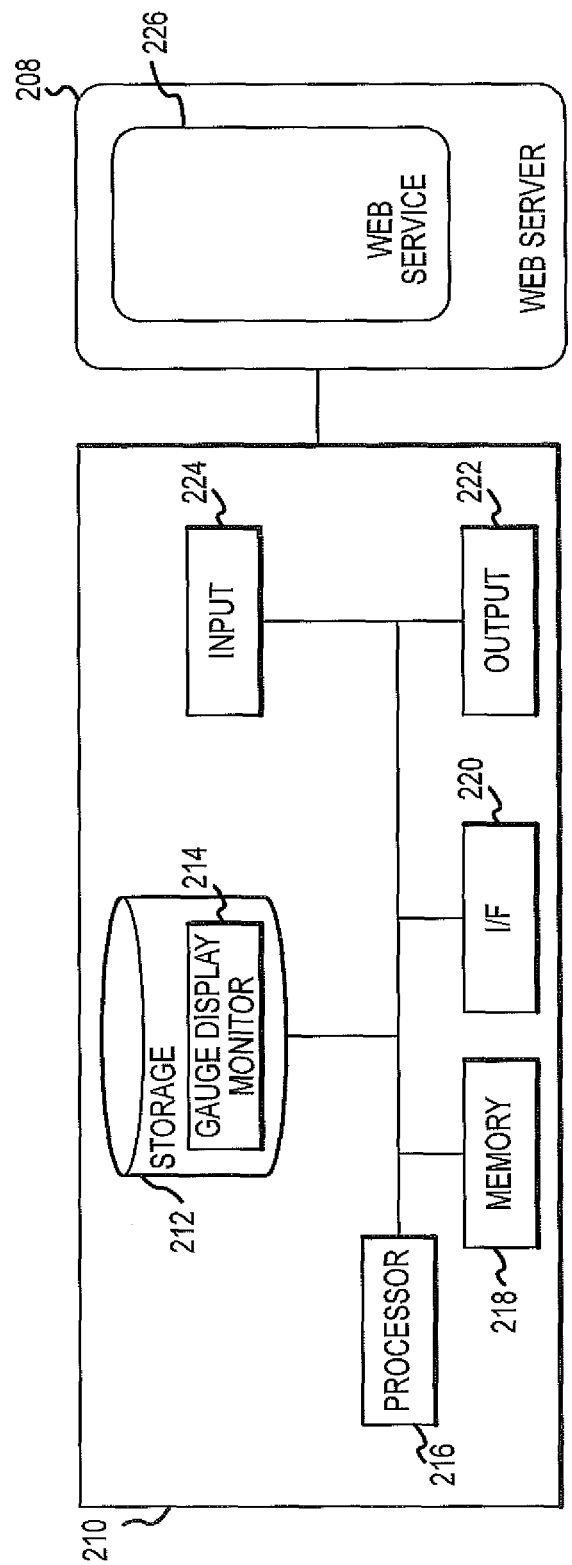
FIG. 2 illustrates an example remote device of the system for patient monitoring in FIG. 1, according to certain embodiments of the present disclosure.

FIG. 2 illustrates an example remote device of the system for patient monitoring in FIG. 1, according to certain embodiments of the present disclosure. Remote device 210 may be substantially similar to remote device 110 of FIG. 1. In FIG. 2, remote device 210 is shown as a mobile telephone communicatively coupled with a web server 208 having a web service 226 capability. Web server 208 may be substantially similar to web server 108 of FIG. 1. Remote device 210 includes a storage device 212, a gauge display monitor 214, a processor 216, a memory 218, a communication interface (I/F) 220, an output device 222, and an input device 224, which are discussed in further detail below. Although this particular implementation of remote device 210 is illustrated and primarily described, the present disclosure contemplates any suitable implementation of remote device 210 according to particular needs.

Storage device 212 may include any suitable device operable for storing data and instructions. Storage device 212 may include, for example, a magnetic disk, flash memory, optical disk, or other suitable data storage device.

Gauge display monitor 214 may include any suitable logic embodied in computer-readable media, and when executed, that is operable to enable a user to communicate with web service 226 on web server 208 to view and manipulate data, including gauge display parameters. For example, gauge display monitor 214 may include logic for receiving data from input device 224 and translating the data into a message to be sent to web service 226 on web server 208, in turn enabling a user to activate a browser and navigate a web page generated by web service 226 on web server 208 to view gauge display parameters. The browser may provide, as part of the gauge display parameters, a summary of all medical devices 102 associated with patients under a caregiver's responsibility, or a detailed view that displays specific medical device 102 configuration data, therapy parameter data, and alarm status data. Gauge display monitor 214 may be configured to cause remote device 210 to request the most recent webpage data from web service 226 on web server 208.

For example, when gauge display monitor 214 requests a parameter (for example, by clicking a navigation link embedded in a display parameter), the browser transmits the request to web service 226. In embodiments with a browser, Web service 226 may extract the request and transmit a copy of the requested parameter in a display parameter format suitable for display by the browser, as well as any required formatting code, such as HTML code, for example. In certain embodiments with a native application, there may not be formatting code. Examples of the browser may include a thick client such as an application, or a thin client browser such as Mozilla (Firefox), Netscape, Internet Explorer, or any future browsers.

Processor 216 may include any suitable device operable to execute instructions and manipulate data to perform operations for gauge display monitor 214. Processor 216 may include, for example, any type of central processing unit (CPU).

Memory 218 may include any computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server). Memory 218 may comprise any other computer-readable tangible medium, or a combination of any of the preceding.

I/F 220 may include any suitable device operable to receive input for gauge display monitor 214, send output from gauge display monitor 214, perform suitable processing of the input or output or both, communicate to other devices, or any combination of the preceding. I/F 220 may include appropriate hardware (for example, a modem, network interface card, etc.) and software, including protocol conversion and data processing capabilities, to communicate through a LAN, WAN, or other communication system that allows gauge display monitor 214 to communicate to other devices. I/F 220 may include one or more ports, conversion software, or a combination of any of the preceding.

Output device 222 may include any suitable device operable for displaying information to a user. Output device 222 may include, for example, a touch screen, a video display, a printer, a plotter, or other suitable output device.

Input device 224 may include any suitable device operable to input, select, and/or manipulate various data and information. Input device 224 may include, for example, a touch screen, a keyboard, mouse, graphics tablet, joystick, light pen, microphone, scanner, or other suitable input device.

Modifications, additions, or omissions may be made to remote device 210 without departing from the scope of the disclosure. The components of remote device 210 may be integrated or separated. Moreover, the operations of remote device 210 may be performed by more, fewer, or other components. For example, although gauge display monitor 214 is displayed as part of storage device 212, gauge display monitor 214 may be stored in any suitable location and the operations of gauge display monitor 214 may be performed by more than one component. Additionally, operations of remote device 210 may be performed using any suitable logic. As used in this document, "each" refers to each member of a set or each member of a subset of a set. Further details of an example remote device 210 are provided below with reference to FIG. 3.

Figure 3:
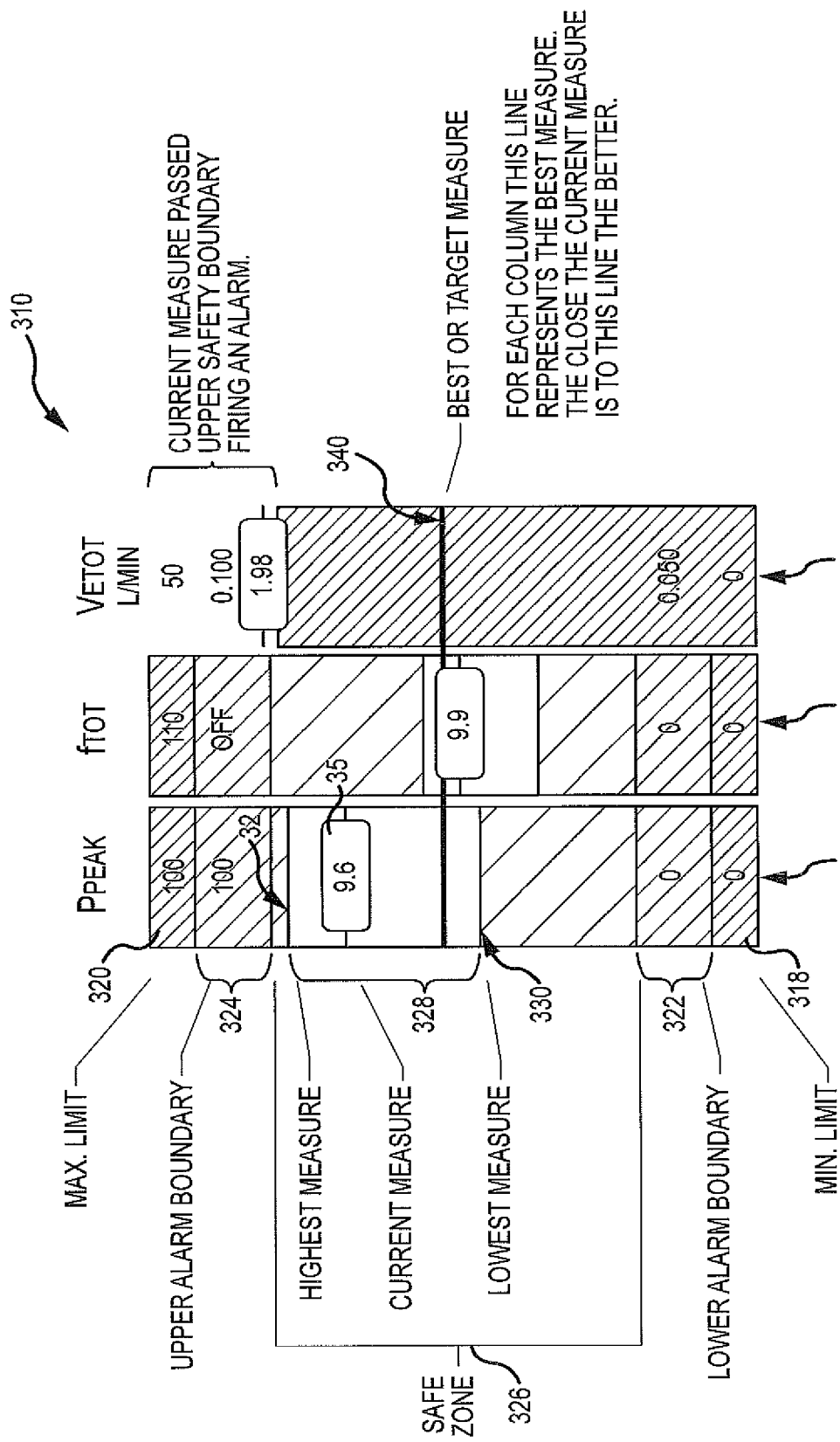
FIG. 3 illustrates an example visual representation of the remote device for patient monitoring in FIG. 1, according to certain embodiments of the present disclosure.

FIG. 3 illustrates an example visual representation 310 of the remote device for patient monitoring in FIG. 1, according to certain embodiments of the present disclosure. In certain embodiments, the visual representation 310 includes example gauge display parameters and can be presented on a display screen of a display device that is communicatively coupled to a ventilator, patient-monitoring device, or other medical device. In certain embodiments, the ventilator or other device can include one or more processors, sensors, and the like, for determining parameter values. In certain embodiments, the ventilator or other device can communicate with any number of computing devices, networks, handheld devices, and the like. In some embodiments, the visual representation 310 can be displayed as part of a user interface that has interactive regions such that a user (e.g., clinician) can access additional information by selecting various interactive regions associated with the visual representation.

The visual representation 310 includes gauge display parameters in the form of bar graphs 312, 314, and 316, each of which displays values of a parameter associated with a ventilator. The bar graph 312 displays values of a peak-pressure parameter; the bar graph 314 displays values of a breath-frequency parameter; and the bar graph 316 displays values of a total-exhalation rate parameter. In some embodiments, additional bar graphs can be included to represent values of other parameters. Additionally, in various embodiments, other types of graphs, charts, and the like, can be used to visually represent values of parameters.

As shown in FIG. 3, each of the bar graphs 312, 314, and 316, includes a number of different regions. For clarity, these regions are described herein with reference to the bar graph 312, but it should be understood that the description (or any part thereof) can be applicable to any number of other bar graphs such as, for example, bar graphs 314 and 316. The bar graph 312 includes a minimum-limit region 318 and a maximum-limit region 320. The minimum-limit section 318 represents a minimum value, or range of values, of the peak-pressure parameter; and the maximum-limit section 320 represents a maximum value, or range of values, of the peak-pressure parameter.

The bar graph 312 also includes a lower-alarm boundary 322 and an upper-alarm boundary 324, each of which represents a value, or range of values, corresponding to an alarm. That is, if a current, measured, value of the peak-pressure parameter falls within the lower-alarm boundary 322 or the upper-alarm boundary 324, an alarm is triggered. In certain embodiments, the boundaries 322 and 324 can be visual representations of parameter-value thresholds. For example, in an embodiment, the lower-alarm boundary 322 represents a set of parameter values including a lower-alarm threshold and any measurable values that are lower than the lower-alarm threshold, but higher than the minimum limit 318. If a current value of the parameter is less than the lower-alarm threshold, an alarm will be triggered, and the current value can be displayed within the lower-alarm boundary 322 of the bar graph 312. Similarly, the upper-alarm boundary 324 can represent a set of parameter values including an upper-alarm threshold and any measureable values that are greater than the upper-alarm threshold and less than the maximum limit 320. In some embodiments, the boundaries 322 and 324 can include threshold values and/or minimum and maximum limits 318 and 320.

As is further illustrated in FIG. 3, the bar graph 312 includes a safe zone 326. In an embodiment, the safe zone 326 includes a range of parameter values that will not cause an alarm to be triggered. In certain embodiments, the safe zone includes all of the represented values between the boundary regions 322 and 324. That is, for example, the parameter values represented by the range of values in the safe zone 326 can be parameter values that are considered to be within normal limits such that immediate medical intervention may not be necessary.

The bar graph 312 also includes an historical range 328. The historical range 328 is a region of the bar graph 312 that represents a range of parameter values that have been measured over the course of some time period. The range 328 is defined, at a lower end, by a lowest-measured value 330 and, at an upper end, by a highest-measured value 32. According to various embodiments, the visual representation 310 can be configured to display an historical range 328 representing any desirable time period. For example, in some embodiments, the historical range 328 represents the range of values measured from the time that the ventilator was activated. In other embodiments, the historical range 328 represents the range of values measured over the course of predetermined (or, in certain embodiments, dynamically determined) time interval, or the like. In some embodiments, the historical range 328 can include values within either, or both, of the boundary regions 322 and 324.

A current value 35 is also displayed in the visual representation 310. As shown, the current value 35 can be displayed within the historical range 328. In certain embodiments, the historical range 328 can represent a set of values that was measured during a previous time interval, in which case, the current value 35 may be displayed at a position outside of the historical range 328.

According to some embodiments of the invention, the bar graphs 312, 314, and 316 can also include other features that can be displayed within (e.g., superimposed on) the visual representation 310. For example, in certain embodiments, a waveform can be displayed on a bar graph 312, 314, 316. In certain embodiments, the waveform can be displayed within the historical region 328, while, in other embodiments, the waveform can be displayed in other regions. In some embodiments, gradient coloration bands can be used to indicate parameter value averages, levels of severity, and the like.

As shown in FIG. 3, the visual representation 310 can also include a target-value indicator 340 that represents a parameter value associated with a desirable patient or operation condition. In certain embodiments, as shown, the target-value indicator 340 can include a horizontal line that crosses one or more of the bar graphs 312, 314, and 316. In the illustrated embodiment, the target-value indicator 340 includes a horizontal line that intersects each of the bar graphs 312, 314, and 316 at or near the center of the safe zone 326. Although each of the bar graphs 312, 314, and 316 and associated ranges and values may represent gauge display parameters of different types (e.g., parameters having different units, value ranges, etc.), the bar graphs 312, 314, and 316 can be scaled such that the target value associated with each parameter is located along the target-value indicator 340.

In some embodiments, any number of various color and/or shading schemes can be used to represent various metrics associated with the parameter values. For example, in certain embodiments, varying color intensities can represent varying frequencies associated with parameter values. For instance, an historical range 328 can be configured to represent data captured over a period of several hours, in which multiple instances of a given parameter value can be observed. Within the historical range 328, varying colors, color shades, and/or color intensities can be used to represent a relative frequency of these observations. In one example, a darker color associated with a given value might indicate that the value was observed relatively infrequently with respect to other values, while a lighter color might indicate that the value was observed relatively frequently with respect to other values. Any number of other metrics associated with a parameter can be represented in various similar ways, as well, such as a data age or trend may be indicated using, for example, darker shading for older data points and lighter shading for newer data points.

Figure 4:
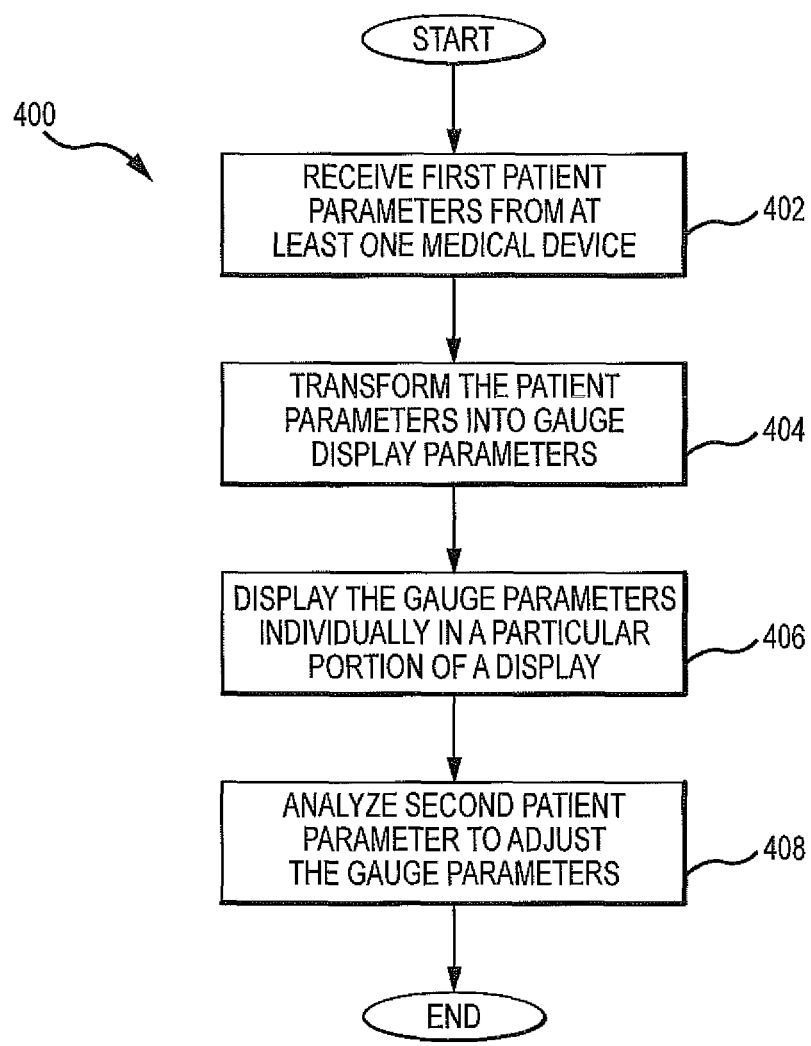
FIG. 4 illustrates an example method for patient monitoring, according to certain embodiments of the present disclosure.

FIG. 4 illustrates an example method 400 for patient monitoring, according to certain embodiments of the present disclosure. Method 400 begins at step 402 where one or more first patient parameters are received from at least one medical device. At step 404, the one or more first patient parameters are transformed into one or more gauge display parameters. At step 406, data operable to display the one or more gauge display parameters individually in a particular portion of a display device are generated. The one or more gauge display parameters include at least a historical range and a current value within the historical range as described above in FIG. 3. At step 408, one or more second patient parameters are analyzed to adjust the one or more gauge display parameters. In some embodiments, the display parameters may be updated such that a visual representation of historical parameter values and current parameter values are provided and a parameter value may be displayed relative to representations of predetermined limits, as well as a range of parameter values that have been observed over a period of time. In certain embodiments, the one or more gauge display parameters may comprise at least one value indicating a physiological condition and at least one of an acceptable threshold related to the value indicating a physiological condition, a unit of measurement related to the value indicating a physiological condition, and an alarm state related to the value indicating a physiological condition.

Although this disclosure has been described in terms of certain embodiments, alterations and permutations of the embodiments will be apparent to those skilled in the art. Accordingly, the above description of the embodiments does not constrain this disclosure. Other changes, substitutions, and alterations are possible without departing from the spirit and scope of this disclosure, as defined by the following claims.

What is claimed is:

1. A method, comprising the steps of:
    receiving one or more first patient parameters from at least one medical device;
    transforming the one or more first patient parameters into one or more gauge display parameters;
    generating data operable to display the one or more gauge display parameters individually in a particular portion of a display device, the one or more gauge display parameters comprising at least a historical range and a current value within the historical range, the historical range comprising a particular color indicative of a frequency of observations; and
    analyzing one or more second patient parameters to adjust the one or more gauge display parameters.

2. The method of claim 1, wherein the one or more gauge display parameters comprise one or more bar graphs.

3. The method of claim 1, wherein the one or more gauge display parameters comprise a lower-alarm boundary and an upper-alarm boundary.

4. The method of claim 1, wherein the one or more gauge display parameters comprise a safe zone that includes a range of parameter values that will not cause an alarm to be triggered.

5. The method of claim 1, wherein the one or more gauge display parameters comprise a waveform.

6. The method of claim 1, wherein the one or more gauge display parameters comprise a target measure.

7. A system, comprising one or more processing units operable to:

receive one or more first patient parameters from at least one medical device;

transform the one or more first patient parameters into one or more gauge display parameters;

generate data operable to display the one or more gauge display parameters individually in a particular portion of a display device, the one or more gauge display parameters comprising at least a historical range and a current value within the historical range, the historical range comprising a particular color indicative of a frequency of observations; and analyze one or more second patient parameters to adjust the one or more gauge display parameters.

8. The system of claim 7, wherein the one or more gauge display parameters comprise one or more bar graphs.

9. The system of claim 7, wherein the one or more gauge display parameters comprise a lower-alarm boundary and an upper-alarm boundary.

10. The system of claim 7, wherein the one or more gauge display parameters comprise a safe zone that includes a range of parameter values that will not cause an alarm to be triggered.

11. The system of claim 7, wherein the one or more gauge display parameters comprise a waveform.

12. The system of claim 7, wherein the one or more gauge display parameters comprise a target measure.

13. Logic embodied in at least one tangible, computer-readable medium and when executed operable to:

receive one or more first patient parameters from at least one medical device;

transform the one or more first patient parameters into one or more gauge display parameters;

generate data operable to display the one or more gauge display parameters individually in a particular portion of a display device, the one or more gauge display parameters comprising at least a historical range and a current value within the historical range, the historical range comprising a particular color indicative of a frequency of observations; and analyze one or more second patient parameters to adjust the one or more gauge display parameters.

14. The logic of claim 13, wherein the one or more gauge display parameters comprise one or more bar graphs.

15. The logic of claim 13, wherein the one or more gauge display parameters comprise a lower-alarm boundary and an upper-alarm boundary.

16. The logic of claim 13, wherein the one or more gauge display parameters comprise a target measure.

17. The logic of claim 13, wherein the one or more gauge display parameters comprise a safe zone that includes a range of parameter values that will not cause an alarm to be triggered.

18. The logic of claim 13, wherein the one or more gauge display parameters comprise a waveform.

\* \* \* \* \*